(12) United States Patent
Berke

(10) Patent No.: US 6,336,917 B1
(45) Date of Patent: Jan. 8, 2002

(54) OCULAR INSPECTION AND EYE MIST APPARATUS

(75) Inventor: Joseph J. Berke, West Bloomfield, MI (US)

(73) Assignee: Nulli Secundus, Inc.

( * ) Notice: Subject to any disclaimer, the term of this patent is extended or adjusted under 35 U.S.C. 154(b) by 0 days.

(21) Appl. No.: 09/018,578

(22) Filed: Feb. 4, 1998

(51) Int. Cl.$^7$ .............................................. A61M 35/00
(52) U.S. Cl. ....................................... 604/295; 604/294
(58) Field of Search ................................ 604/294, 295, 604/296, 300, 301, 302; 222/383.1, 523, 525, 526, 527, 419, 420

(56) References Cited

U.S. PATENT DOCUMENTS

| | | | | |
|---|---|---|---|---|
| 2,209,192 A | * | 7/1940 | Demsey ...................... 604/300 |
| 3,170,462 A | * | 2/1965 | Hall ........................... 604/300 |
| 4,685,906 A | * | 8/1987 | Murphy ...................... 604/300 |
| 4,701,167 A | * | 10/1987 | Chekan ....................... 604/301 |
| 4,792,334 A | | 12/1988 | Py |
| 4,946,452 A | | 8/1990 | Py |
| 4,960,407 A | | 10/1990 | Cope |
| 5,267,986 A | | 12/1993 | Py |
| 5,295,981 A | * | 3/1994 | Smith et al. ................ 604/301 |
| 5,588,564 A | * | 12/1996 | Hutson et al. ............ 222/383.1 |
| 5,607,410 A | * | 3/1997 | Branch ....................... 604/302 |
| 5,611,788 A | | 3/1997 | Marchment ............................ |

* cited by examiner

*Primary Examiner*—Kim M. Lewis
(74) *Attorney, Agent, or Firm*—Foley & Lardner

(57) ABSTRACT

An ocular inspection and treatment eye mist apparatus having an outer housing that contacts the bony orbit surrounding the eye. An inner housing, concentrically disposed within the outer housing contacts the eyelid, pushing the eyelid back, exposing the eye. The outer housing is adjustable longitudinally over the inner housing to accommodate different users. The position of the outer housing prevents the inner housing from protruding too far into the eye by acting as a stop against the bony orbit. One end of the inner housing is adapted to receive a dispenser for administering a metered spray of medicine, powdered or liquid, or lavage to the eye as it is held open by the ocular treatment apparatus. The dispenser nozzle is equipped with a contrasting mark which provides a target for the eye to focus on ensuring the eye is optimally positioned to receive the metered spray. A method of using the ocular apparatus for inspecting the eye or administering a medication or lavage to the eye including adjusting the inner and outer housings, positioning the apparatus on the eye to have the inner housing contact the eyelids peri-occularly to retract the eyelids and to have the outer housing contact peri-orbitally to act as a stop.

12 Claims, 2 Drawing Sheets

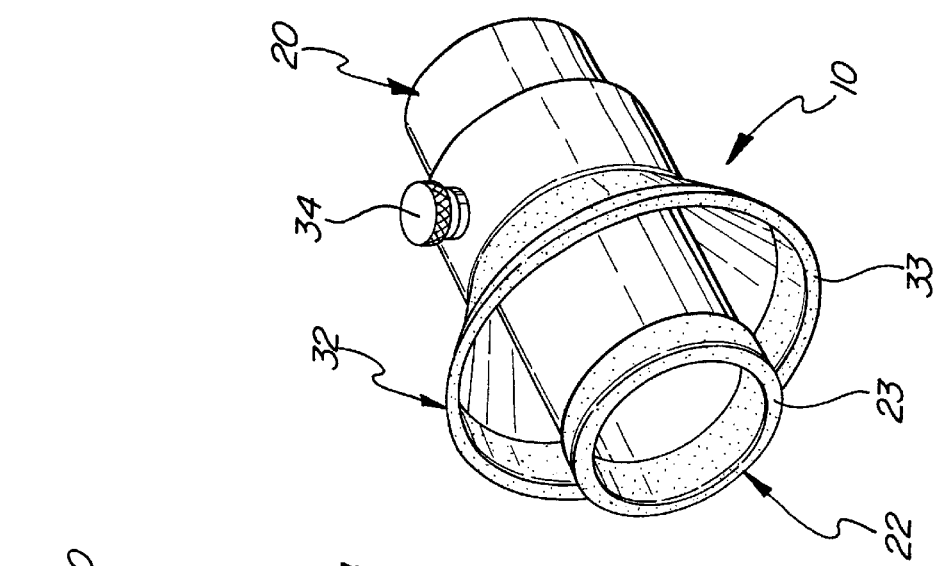
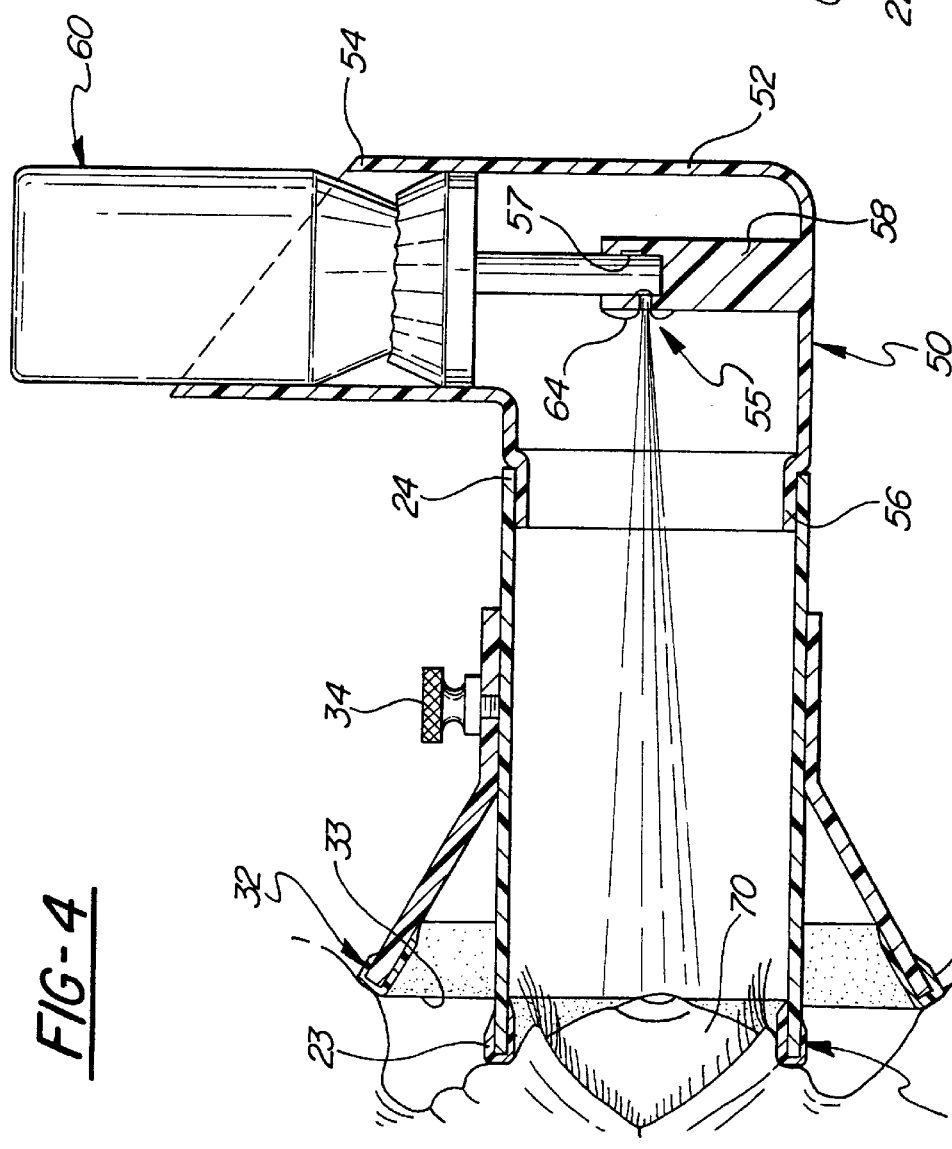

OCULAR INSPECTION AND EYE MIST APPARATUS

BACKGROUND OF THE INVENTION

1. Field of the Invention

This invention relates to an ocular eye treatment and inspection speculum, namely a metered spray eye mist apparatus and a method of operation therefor. In particular, this invention relates to an eye mist apparatus for fixing open the eyelids and fixing the eyeball in spot for inspection or administering a metered amount of medication to the eye.

2. Description of the Prior Art

Inspecting and treating the human eye, and in particular applying medicine to the eyeball, is a sensitive and usually difficult task. The eye is a very sensitive area of the body and it is often difficult for someone, such as a physician, ophthalmologist or oculist, to treat and inspect the eye because a patient is unable to comfortably maintain his or her eyelids in an open, unblinking, position. Additionally, the body reacts such that it causes tears to be produced and the eye retracts when the eye lids are forced open or fixed for an extended period of time. Even more complicating to personally administering medicine can be the lack of motor skills, arthritis or disability due to age.

In the past, medications and irrigations for the eye have been applied as drops on the eye's anterior surface, which requires a steady hand for holding and applying the medicine, as well as a flexible neck for moving the head and positioning the eye to accept the medication. The process is usually difficult and messy. This is especially true for elderly people, who are more likely to require medications of this type. Medications and irrigations are frequently required for individuals with glaucoma, infections such as conjunctivitis (red-eye), injuries to the eyes or contact lens wearers.

There have been several developments to assist patients in applying medication to the eye. These prior developments focus on easing the application of a drop of liquid medication onto the eye's surface. For example, U.S. Pat. Nos. 4,960,407 to Cope; 5,611,788 to Marchment; 4,792,334 to Py; 4,946,452 to Py; and 5,267,986 to Py, each disclose an apparatus that fits over a nozzle of an eyedropper. The apparatuses disclosed in each of these patents has a contoured opening to fit around or within the peri-orbital area of the eye of the patient. These devices hold the eyelids open so the medicine can supposedly drip freely onto the eye's surface. However, it is not uncommon for the drops to miss the eye, or for the contoured opening to improperly hold the eyelids open. Either way, the drop of medicine is not administered to the anterior surface of the eye.

Alternatively to the above, there have been attempts to redirect the drop and apply it to a specific point of the eye. For example, the Marchment reference discloses a flange that bears against the patient's face and pushes the lower eyelid downward so the eyedrops are dispensed into the lower portion, or cul-de-sac, at the very lowest portion of the anterior surface of the eye. Likewise, the 4,946,452 reference to Py discloses a flexible bar adapted to engage the facial tissue below the eye, displacing the lower eyelid and dispensing the medicine directly into the cul-de-sac of the eye.

The problem with devices of this type is they require a significant amount of manual dexterity to position the apparatus over the eye, and a steady hand to maintain the apparatus over the eye. Additionally problematic, the above devices require patients to tilt their head back so the medicine bottle is in a vertical position, allowing the drop to fall into the eye by force of gravity. This is often difficult for elderly arthritic patients who experience difficulty moving the neck, or have weak and unsteady hands.

Significantly, all of these prior art apparatuses dispense the medicine in a drop. There are several drawbacks associated with dispensing eye medicine as a drop. It is difficult to control the drop size, and the number of drops (i.e., the amount of medicine applied to the eye). It is also difficult to evenly distribute the medicine over the entire anterior surface of the eye, thereby reducing the effectiveness of the medication and slowing any effective healing process.

The use of conventional eye droppers makes it difficult to control the quantity of medicine applied to the eye. Too much medicine simply spills over the eyelid making the application messy and costly. Not getting enough medicine administered to the eye will result in incomplete treatment, possibly extending the patient's discomfort.

Prior art devices dispense a drop of medicine or fluid onto the eye, or into the cul-de-sac of the eye, where it travels directly along the excretory path of the eye and out the tear ducts. Much of the medicine is lost through the tear ducts as soon as it is applied to the eye, or remains in the cul-de-sac where it cannot be distributed over the eye's surface by blinking.

In some of the above mentioned references, there is no way for prior art devices to control locating the opening of the dispenser properly over the eye socket. For example, the dispenser could be pushed directly into the eyeball possibly causing injury to the eye. The 5,267,986 reference to Py has a finger-like projection that could easily cause damage to the eye if not accurately and properly located. A sudden, unexpected movement by the user could result in the projection injuring the eyeball.

Thus, there remains a long felt, significant and unfulfilled need for an ocular treatment and inspection apparatus that does not require extensive manual dexterity to position and operate, simplifying the application of medicine to the eye. The apparatus must not have any potentially damaging projections and somebody with a weak or unsteady hand must be able to operate the apparatus with ease, and without the potential for injury. Likewise, the apparatus must be capable of being used for other treatments to the eye; for example, viewing the eye during an ocular examination, looking for a foreign object in the eye, or in conjunction with glaucoma testing. There is also a need for an ocular treatment apparatus that is capable of dispensing medicine (in different forms) in the eye in an effective, accurate and measured manner.

SUMMARY OF THE INVENTION

The present invention relates generally to an ocular treatment and inspection apparatus that opens the eyelid and fixes the eyeball in spot for treating the eye by dispensing medicine into the eye or for simply viewing the eye. When the ocular treatment apparatus is used as a medicine dispenser, the medicine is dispensed as a metered spray, mist or dispersed powder for more accurate and thorough coverage of the eye's surface with less waste than medicine applied in drop form. The present invention is also capable of being used in conjunction with standard glaucoma tests because it opens and fixes the eye for the patient without discomfort.

The ocular treatment and inspection apparatus of the present invention preferably includes an inner housing having a peripheral edge for engaging and conforming with the eyelids and the eyeball. The peripheral edge of the inner housing opens the eyelids and fixes the eyeball in spot by making peri-ocular contact about the outside of the eyelids over the eye. The eyelids are retracted off of the eye, exposing the anterior surface of the eyeball.

The inner housing has an opening therethrough. A peri-ocular end of the inner housing is placed over the eye, as described above, and the opposite end of the inner housing is used to view the eye or it can be adapted to receive a medicine or fluid dispenser.

An outer housing, also having a peripheral edge, is concentrically aligned with the inner housing. The peripheral edge of the outer (or peri-orbital) housing conforms to the bony orbit surrounding the eye. The outer housing holds the entire ocular treatment apparatus in place over the eye. The ocular treatment and inspection apparatus rests against the bony peri-orbital region surrounding the eye, instead of directly on the soft tissue surrounding the eye, or the eyeball itself.

The outer, peri-orbital housing acts as a stop against the bony, peri-orbital region allowing the inner housing to enter only a predetermined distance into the eye socket, protecting the soft tissue around the eye and the eyeball itself from intrusion by the inner housing. The longitudinal position of the outer housing relative to the inner housing is adjustable for individual users and can be set by a set screw or any other similar device which will maintain the relative position of the inner and outer housing thereby preventing the inner housing from protruding too far into the eye socket.

The inner housing preferably is shaped to draw the lower portion of the eyelid away from the eye by having an angled profile on the peri-ocular end of the inner housing. The upper portion of the inner housing first contacts the upper part of the eyelid since it is longer than the lower portion of the inner housing which contacts the lower part of the eyelid, accomplishes this objective.

The peripheries of ends of the inner and outer housings are coated with a hypo-allergenic, rubber or latex material to prevent the apparatus from slipping on the skin due to oils and tears on the skin. The hypo-allergenic material is safe to the skin and aids the user in holding the ocular treatment apparatus in place over the eye. The coating also provides a surface softer than the hard plastic housing for contacting the skin, making the ocular treatment apparatus comfortable.

In one embodiment of the present invention, the ocular treatment apparatus dispenses medicine into the eye. The portion of the dispenser that releases and directs the medication or fluid fits into one end of the inner housing. The body of the dispenser is preferably bent at an angle relative to a medicine vial so pressure applied to the dispenser in a vertical direction releases medicine in a horizontal path and is applied directly onto the surface of the eye. This eliminates the need to contort the head and neck to allow medicine to "drop" vertically into the eye as required by conventional eyedrops.

The medicine dispenser of the present invention is used in conjunction with a medicine vial similar to an inhaler used by asthmatics in that it dispenses a metered spray of medication or fluid by applying pressure to a medicine vial disposed within the dispenser. The spray of medicine is applied evenly over the surface of the eye. The quantity and application of medicine to the eye can be strictly controlled, thereby eliminating messy drips and spillage. Additionally, the spray mist presents a more thorough coverage than a drop dispensed into the cul-de-sac of the eye where it mixes with tears and runs directly out the tear ducts of the eye.

The medicine dispenser is rotatably mounted to the inner housing for positioning at any position comfortable for the user. This is especially convenient for both left handed and right handed people administering medication in both eyes.

In another embodiment of the present invention in which the ocular treatment and inspection apparatus is primarily used to view the eye, a handle is rotatably mounted to either the inner or outer housing. The handle allows a physician, attendant or even the patient to hold the ocular treatment apparatus in a comfortable position conducive to effectively viewing the eye.

Accordingly, it is an object of the present invention to provide an ocular treatment and inspection apparatus capable of being used in an upright position eliminating the need for users to tilt their head in an awkward position to administer medicine.

It is an object of the present invention to provide an ocular treatment apparatus that is easy and safe to use.

It is another object of the present invention to provide an ocular treatment apparatus that is capable of being used to view the eye, dispense medicine into the eye, or to provide treatment to the eye in which the apparatus has a first inner housing having a peri-ocular end and a second outer housing having a peri-orbital end.

It is yet another object of the present invention to provide an ocular treatment apparatus that can apply medicine horizontally to the eye in a uniform, effective manner.

It is a further object of the present invention to provide an ocular treatment apparatus that is adjustable to suit individual user's needs showing a color-coded fixation feature.

Other advantages of the present invention will become more apparent from the following detailed description of the preferred embodiment taken in conjunction with the accompanying drawings.

BRIEF DESCRIPTION OF THE DRAWINGS

FIG. 3 is a perspective view of the ocular treatment apparatus of the present invention; and FIG. 4 is a side view shown in partial cross section of the ocular treatment apparatus of the present invention shown in an embodiment in which the apparatus is being used to dispense medicine or fluid into an eye.

DETAILED DESCRIPTION OF THE PREFERRED EMBODIMENT

Figure 1:
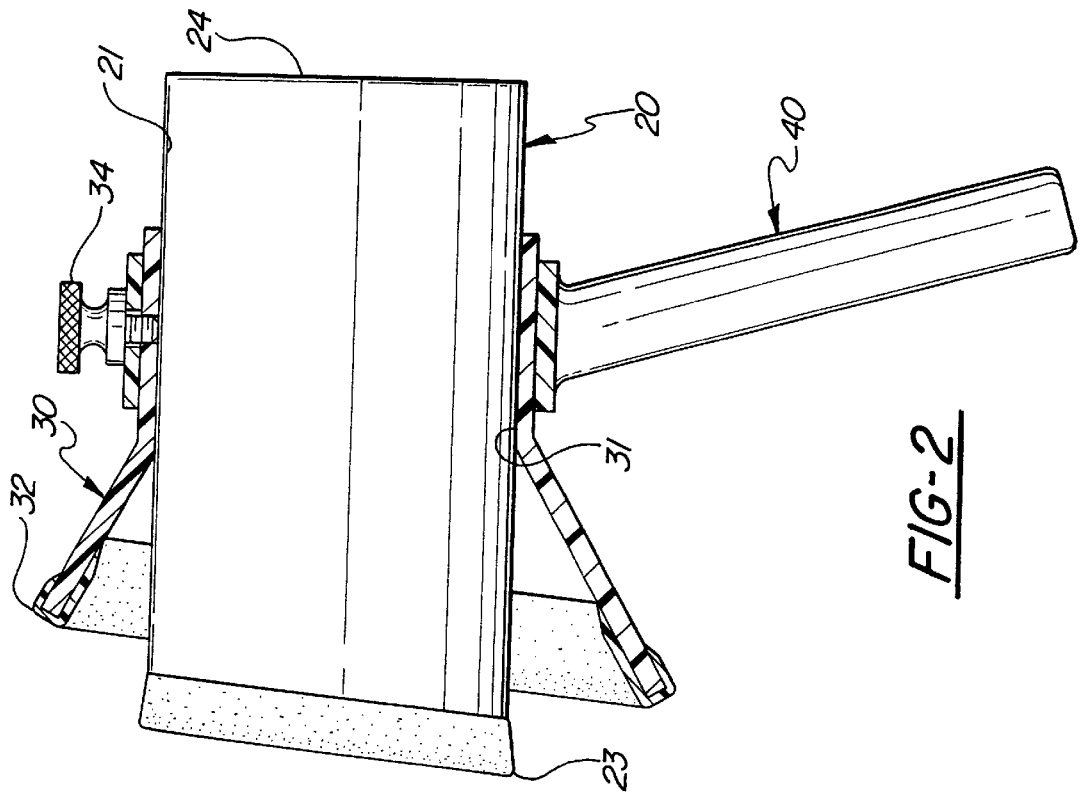
FIG. 1 is a side view shown in partial cross section of an ocular speculum apparatus according to the present invention.

Referring generally to FIGS. 1 through 4, an ocular treatment apparatus 10 of the present invention is shown. The ocular treatment apparatus 10 includes a first or inner housing 20 having an opening 21 therethrough. A peri-ocular end 22, of the inner housing 20 has a peripheral edge 23 for making peri-ocular contact where it contacts the eyelid and surrounding the eyeball.

An outer housing 30 is concentrically aligned with the inner housing 20. A peri-orbital end 32 of the outer housing 30 has a peripheral edge 33 for making peri-orbital contact where it contacts the skin over the bony orbit surrounding the eye. The peripheral edge 33 of the outer housing 30 has a larger diameter than the peripheral edge 23 of the inner housing 20. The outer housing 30 narrows to a diameter defining an opening 31 that is just slightly larger than the diameter of the inner housing 20 so that it can rotate around and slide along the inner housing 20. The outer housing 20 can be fixed at any desired location by a set screw 34, or any other suitable fastener or means for fixing the outer housing 30 with respect to the inner housing 20.

The outer housing 30 moves longitudinally along the inner housing 20 so that the outer housing 30 can be adjusted with respect to the inner housing 20 to a position desired for each individual user. The inner housing 20 is designed to engage the eyelids of the user and retain the upper and lower eyelids open and fix the eyeball in spot. The outer housing 30 aligns and holds the inner housing 20 in place over the eye. The position of the peri-orbital end 32 and peripheral edge 33 of the outer housing 30 is set by a set screw 34 to a predetermined distance relative to the peri-ocular end 22 and peripheral edge 23 of the inner housing 20. The position of the outer housing 30 relative to the inner housing 20 is set as a function of the geometry of the individual's eyeball, bony orbit and relevant facial features. The outer housing 30 is likely to be adjusted for each user.

FIG. 4 shows the peri-ocular end 22 of the inner housing 20 contacting the eyelid 72 and pushing it open and holding the eyeball 70 in spot. However, the peri-ocular end 22 does not contact the eyeball 70 directly. The peri-orbital end 32 of the outer housing 30 rests against the bony orbit 74 surrounding the eyeball 70. Pressure is applied by a user or an attendant (such as a physician) to hold the apparatus in place over the eye 70 such that the peri-orbital end 32 of the outer housing 30 and not the peri-ocular end 22 of the inner housing 20 carries the significant majority of the pressure. The peri-orbital end 32 of the outer housing 30 stops the inner housing 20 at the desired position where the peripheral edge 23 of the peri-ocular end 22 merely applies sufficient pressure to hold open the eyelid 72. Thus, it is not possible to insert the ocular treatment apparatus 10 too far into the eye where it could cause discomfort or possibly damage the eyeball 70.

Figure 2:
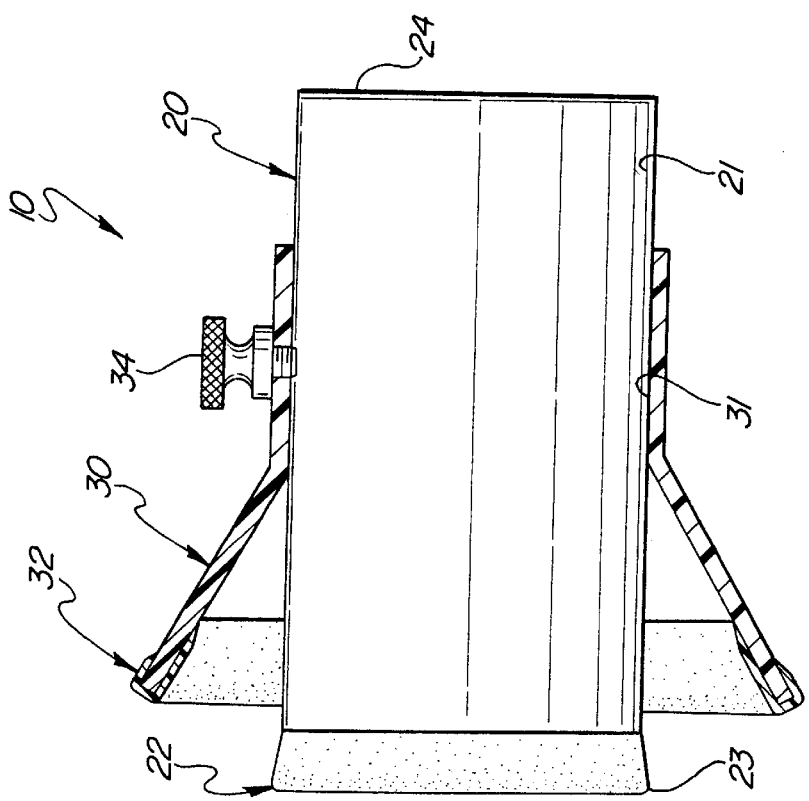
FIG. 2 is a side view shown in partial cross section of the ocular treatment apparatus of the present invention showing an angled profile of the peri-ocular end of the inner housing. A handle mounted to the outer housing is also shown.

In the embodiment shown in FIG. 2, the ocular treatment apparatus includes a handle 40 connected to the outer housing 30. The handle 40 rotates relative to the inner 20 and outer 30 housings and can be fixed to any position desired by the user by the set screw 34. The handle 40 makes it convenient for a user, i.e. the patient or the physician, to grip the ocular treatment apparatus 10 and hold it steady for viewing the eye or for administering medication.

FIG. 3 shows an alternate embodiment of an ocular inspection device according to the present invention including an angled profile for the peripheral edge 23 of the peri-ocular end 22 of the inner housing 20. The portion of the peripheral edge 23 of the inner housing 20 that contacts the eyelid below the eyeball 70 is extended so that the lower portion of the eyelid is pushed back further than the upper portion of the eyelid, exposing more of the surface of the eye. This is advantageous because when medicine is applied to the eye's surface more complete coverage of the eye can be achieved because a larger surface area of the eye can be seen. Accordingly, more complete viewing of the eye can also be obtained.

The peri-ocular end 22 and the peri-orbital end 32 of the present invention are preferably coated with a rubber latex material 80 as shown in FIGS. 1 through 4. The rubber latex provides a soft surface that contacts the delicate skin surrounding the eye making it more comfortable to use the apparatus 10 according to the present invention. Additionally, the rubber material provides a non-slip surface that grips the eyelid and skin surrounding the eye for a stable positioning of the apparatus 10 over the eye.

Referring to FIG. 4, an alternate embodiment of the ocular treatment apparatus 10 according to the present invention is shown in which the apparatus 10 administers medicine to the eye 70. An end 24 of the inner housing 20 opposite the peri-ocular end 22 receives a medicine dispenser 50 for administering medicine to the eye 70. The dispenser 50 includes a body 52 having a first end 54 and a second end 56 at substantially right angles to each other. The first end 54 receives a vial 60 of medicine. The second end 56 is inserted into the end 24 of the inner housing 20 to convey the medicine within the vial 60 into the eye 70.

The second end 54 of the dispenser body 52 is preferably at substantially a right angle to the first end 52 such that the medicine to be dispensed onto the eye 70 is administered horizontally directly onto the eye's anterior surface without having to contort the head and neck.

In yet a further alternate embodiment to the present invention, the apparatus 10 is provided with a contrasting mark 64 surrounding an outlet or hole 59 of the dispenser 50 at which the medicine is released from the dispenser body 52 provides a target for the user to focus upon. The contrasting mark 64 can be a color coded ring, including three dimensional aspects, or other distinguishing indicia, that can be easily focused upon so when the ocular treatment apparatus is properly positioned over the eye and the eye is directed to focus on the contrasting mark 64. By focusing the eyeball to be directed upon the contrasting mark 64 the eyeball 70 is positioned to receive the optimum amount of medicine, or lavage treatment.

A post member 58 is located within the body 52 of the dispenser 50. The post member 58 has an opening 57 for receiving a nozzle 62 of the medicine vial 60. The hole 59 on the lpost member 58 is located transverse to the opening 57. In operation, pressure is applied to the vial 60 depressing the nozzle 62 releasing a predetermined, or metered, amount of medicine. The medicine or fluid lavage (the medicine or lavage can be in any form such as a powder, liquid, gas, solid or any combination of the above) travels through the tubular member 58 and exits through the hole 59 preferably as a mist directed through the inner housing 20 and onto the eye's surface. The appartus 10 is preferably designed such that the medicine or lavage is sprayed or dispensed to be directed at only the anterior surface of the eyeball 70 although it is possible to cover more than just the eyeball 70.

As previously explained, the peri-ocular end 22 of the inner housing 20 holds the eyelid 72 in an open position exposing the eyeball 70. It is not possible for medicine to escape the ocular treatment apparatus 10, and this waste is avoided. All of the medicine dispensed in the metered spray is evenly distributed directly onto the anterior surface of the eyeball 70, thereby ensuring an appropriate amount of medicine is administered to the eyeball 70. The peri-orbital end 32 of the outer housing 30 rests against the bony orbit 74 securing the ocular treatment apparatus 10 comfortably in place over the eye to protect the eyeball 70, as previously disussed.

One significant advantage of the apparatus 10 according to the present invention is that medicine or a fluid lavage can be applied to the eyeball using only one hand. The ocular treatment apparatus 10 is attached to the dispensing or second end 56 of the dispenser 50 and can be held against the bony orbit 74 while depressing the vial 60 with the same hand.

It should also be noted it is possible and convenient to use the ocular treatment apparatus 10 of the present invention in conjunction with standard glaucoma tests. Typically, the patient is asked to hold their eye open to receive a blast of air that is used to measure pressure in the eye and provides an indication of glaucoma. It is a very uncomfortable procedure because it is extremely difficult to hold open the eye without blinking, which is a compulsory bodily function. Due to the sensitive nature of the eye, it is even more difficult to hold the eye open when it is expected to receive a blast of air. The ocular treatment apparatus 10 of the present invention safely and comfortably holds the eyelid in an open position, exposing the eyeball, and preventing a user from blinking.

As shown in FIG. 4, the outer housing 30 rests comfortably against the bony orbit 74 surrounding the eye 70 and does not allow the inner housing 20 to protrude too far into the eye 70. The ocular treatment apparatus 10 of the present invention does not have protruding members, or fingers that contact the user's face where they present the potential for injury. Therefore, even a sudden, unexpected movement by the patient will not result in the apparatus causing injury to the eye.

Because the device is simple to use and is easily and safely stabilized over the eye, it is capable of being used by users having unsteady hands or other disabilities, without fear of injury to the eye or the user in general. This feature in conjunction with the one-handed operation of the device makes it especially applicable to elderly users who are no longer capable of bending their head back or maintaining their eyes open.

While the invention has been set forth and described in terms of a preferred embodiment, it is apparent that other forms of the present invention can be adopted by one skilled in the art. For example, any type of fastening means between the inner and outer housing 5 can be used. Further, a unitary housing can be used provided it has a peri-orbital edge and a peri-ocular edge. Other types of uses for the present device such as incorporation of a light for viewing the eye are also possible. Accordingly, the scope of the present invention is limited only by the following claims.

What is claimed is:

1. An ocular apparatus for preparing an eyelid and inspecting an eyeball located on a face having a bony orbit proximate the eyeball, said ocular treatment apparatus comprising:

an inner housing member having a first end and a second end, said first end having a peripheral edge defining an opening therein, said peripheral edge being shaped for engaging and retracting the eyelid in an open position and fixing the eyeball in spot; and an outer housing member having a first end having a peripheral edge defining an opening therein, said peripheral edge of said outer housing member capable of corresponding to the bony orbit defining an orbit surrounding the eyeball, said peripheral edge of said outer housing member concentric with said peripheral edge of said inner housing member, said peripheral edge of said outer housing member being adjustable in relation to said peripheral edge of said inner housing member such that said inner housing member protrudes a predetermined distance into the orbit thereby avoiding injury to the eyeball.

2. An ocular treatment apparatus according to claim 1 further comprising a dispenser mounted to said second end of said inner housing, said dispenser for receiving a vial of medicine, powder or lavage for irrigation, pressure applied to said vial causes said dispenser to release a predetermined amount of said medicine onto the eyeball in the form of a metered spray.

3. An ocular treatment apparatus according to claim 1 wherein said outer housing member is rotatably mounted to said inner housing member.

4. An ocular treatment apparatus according to claim 3 wherein said outer housing member further comprises a handle.

5. An ocular treatment apparatus according to claim 3 wherein said outer housing member is adjustable longitudinally along said inner housing member for adjusting said predetermined distance from said inner housing member enters the orbit.

6. An ocular treatment apparatus according to claim 5 further comprising means for fixing said outer housing member in position on said inner housing member.

7. An ocular treatment apparatus according to claim 1 wherein said peripheral edge of said inner housing member further comprises a non-slip surface coating.

8. An ocular treatment apparatus according to claim 1 wherein said peripheral edge of said outer housing member further comprises a non-slip surface coating.

9. An ocular treatment apparatus according to claim 7 further comprising a non-slip surface coating on said peripheral edge of said outer housing member.

10. An ocular treatment apparatus according to claim 1 wherein said peripheral edge of said inner housing member is angled defining a leading edge for fixing said eyeball in spot.

11. An ocular apparatus for preparing an eyelid and an eyeball for inspecting and treating the eye and eyelid, said ocular treatment apparatus comprising:

(a) a peri-orbital peripheral edge for contacting the peri-orbital region of said eye;

(b) a peri-ocular peripheral edge for contacting the eyelids and fixing the eyeball in spot; and (c) a means for fixing the relative position of said peri-orbital peripheral edge with respect to said peri-ocular peripheral edge.

12. An ocular apparatus according to claim 11 further comprising an outer housing including said peri-orbital peripheral edge, an inner housing including said peri-ocular peripheral edge and wherein said fixing means comprises a threaded member.

* * * * *